United States Patent [19]

McNamara

[11] Patent Number: 5,603,918
[45] Date of Patent: Feb. 18, 1997

[54] AEROSOL COMPOSITION OF A SALT OF IPRATROPIUM AND A SALT OF ALBUTEROL

[75] Inventor: Daniel McNamara, Waterbury, Conn.

[73] Assignee: Boehringer Ingelheim Pharmaceuticals, Inc., Ridgefield, Conn.

[21] Appl. No.: 489,201

[22] Filed: Jun. 9, 1995

[51] Int. Cl.$^6$ .................. A61K 9/12; C09K 3/30
[52] U.S. Cl. .............. 424/46; 252/305; 424/45; 514/929
[58] Field of Search ............ 252/305; 424/45, 424/46; 514/929

[56] References Cited

U.S. PATENT DOCUMENTS 3,219,533  11/1965  Mullins ............... 424/45 X
3,322,625  5/1967   Shimmin ............... 424/45
3,551,558  12/1970  Takebe et al. .......... 424/46
3,644,353  2/1972   Lunts et al. .......... 544/162
4,385,048  5/1983   Mygind et al. ......... 424/45
4,895,719  1/1990   Radhakrishnan et al. .. 424/45

*Primary Examiner*—Richard D. Lovering
*Attorney, Agent, or Firm*—Robert P. Raymond; Mary-Ellen Devlin; Alan R. Stempel

[57] ABSTRACT

The present invention is concerned with an aerosol formulation which contains an effective amount of a pharmaceutically acceptable salt of ipratropium and an effective amount of a pharmaceutically acceptable salt of albuterol in combination with an effective amount of soya lecithin as a suspending agent and a propellant.

14 Claims, No Drawings

AEROSOL COMPOSITION OF A SALT OF IPRATROPIUM AND A SALT OF ALBUTEROL

BACKGROUND OF THE INVENTION

1. Field of the Invention

The present invention provides a novel aerosol composition for inhalation therapy which may be dispensed from standard metered dose aerosol containers.

2. Description of the Related Art

An aerosol for inhalation therapy is a gaseous suspension of very finely divided solid or liquid particles. An aerosol formulation comprises a solution or dispersion of an active ingredient in a liquified medium which comprises a propellant, and any required solvent or surfactant. The propellant is a low boiling liquid, which volatilizes under ambient conditions of temperature and pressure. Aerosol containers for inhalation therapy are provided with metered valves which measure the volume of aerosol dispensed which may be correlated to a particular dose of the medication. These aerosol containers are known as metered dose inhalers (MDI).

In order to deliver an aerosol spray of uniform composition, an aerosol composition should be as homogenous as possible. In addition, it is essential that an aerosol composition be stable under the typical conditions of storage and shipping that are encountered in various populated geographic areas.

It is known in the pharmaceutical art that an inhalation aerosol formulation of a medicament, containing a relatively low boiling chlorofluorocarbon (CFC) as a propellant, such as, for example CFC 12 ($CCl_2F_2$, $T_b/°C.=-29.8$) or CFC 114 ($C_2Cl_2F_4$, $T_b/°C.=3.8$), can be made by first preparing a product concentrate which comprises the active medicament as a finely divided solid, a relatively high boiling CFC, such as for example CFC 11 ($CCl_3F$, $T_b/°C.=23.75$) and a surfactant or suspending agent. This product concentrate can be homogenized at ambient temperature and pressure, using a rotor/stator homogenizer. After the product is homogenized, the homogenized product and the relatively low boiling CFC propellant are introduced into a pressure vessel, where they are mixed to form a completed and homogenous formulation. The completed formulation is then filled into dispensing devices, such as MDI's while working under elevated pressure and ambient pressure (by back filling through the valves of capped containers), or at reduced temperature and ambient pressure (wherein the containers are filled with supercooled formulations and then capped).

In the aforementioned formulation the relatively high boiling CFC serves three important and distinct functions. First, it serves as a solvent for the suspending agent. To ensure accurate, reproducible dosing, it is necessary for the suspending agent to be completely soluble in the product concentrate (in which the high boiling CFC is the only CFC present) and in the entire formulation (in which both high and low boiling CFCs are present). Second, with regard to its interaction with the solid drug particles, the high boiling CFC serves as the dispersion medium. Third, it contributes to the overall vapor pressure of the final formulation. The formulation is one of the variables that affects the optimization of active ingredient deposition in the lungs of a patient and, therefore, the efficacy of the formulation. In this context, the relatively high boiling CFC is referred to as a propellant, because the final vapor pressure of the formulation is the result of the partial pressure contribution of all of the CFCs used in the formulation.

In order to dispense uniform doses of solid drugs, to the lungs the solid particles should be micronized to ensure accurate and reproducible dosing deep into the pulmonary system. Micronization may be accomplished by a milling operation which is carried out before the active substance is incorporated into the formulation. A further criteria which must be considered is the stability of the drug and the suspending agent in the CFCs. If the suspension is unstable and forms agglomerates of drug and suspending agent within a short period of time, it is not possible to redisperse the product because once aggregates form, it is not possible to reliably dispense the metered amounts of the active agent. In addition, the presence of agglomerated particles may interfere with the deposition of the active agent in the lungs by altering the aerodynamic particle size of the active agent.

In the prior art, ipratropium bromide and albuterol (base) have been administered concomitantly from separate aerosol containers for bronchodilation. Teale et al.,in Thorax, 1991;46:287P (Abstr), reported the use of an aqueous mixture of nebulized ipratropium bromide and albuterol (salbutamol) in treatment of chronic obstructive airway disease. The prior art ipratropium bromide aerosol product has included soya lecithin as a suspending agent and the albuterol (base) aerosol has used oleic acid as a suspending agent. Albuterol sulfate has been used orally for bronchodilation in tablet and oral liquid dosage forms as well as in nebulizer solutions.

SUMMARY OF THE INVENTION

The inventor has discovered that a stable, combined aerosol formulation may be prepared which provides the beneficial effects of a pharmaceutically acceptable salt of ipratropium and albuterol (base) if a pharmaceutically acceptable acid addition salt of albuterol is used in place of albuterol (base) with an effective amount of soya lecithin as a suspending agent.

This discovery is surprising and unexpected because aerosol formulations which contain ipratropium bromide and albuterol (base) are unstable and form agglomerates in the presence of soya lecithin or oleic acid within a short time after being prepared.

Accordingly, it is a primary object of the invention to provide an aerosol formulation which permits the simultaneous coadministration of a pharmaceutically acceptable salt of ipratropium and a pharmaceutically acceptable acid addition salt of albuterol.

It is also an object of the invention to provide a stable aerosol formulation of a pharmaceutically acceptable salt of ipratropium and a pharmaceutically acceptable acid addition salt of albuterol which does not form agglomerates.

It is also an object of the invention to provide a formulation of pharmaceutically acceptable salt of ipratropium and a pharmaceutically acceptable salt of albuterol which does not form agglomerates that interfere with the therapeutic activity of either of these drugs when they are simultaneously administered by means of an aerosol formulation.

These and other objects of the invention will become apparent from a review of the appended specification.

DESCRIPTION OF THE PREFERRED EMBODIMENTS

The pharmaceutically acceptable salts of ipratropium are described in U.S. Pat. No. 3,505,337. These salts include the halide salts such as the bromide, chloride and the iodide. The pharmaceutically acceptable salts of albuterol are described in U.S. Pat. No. 3,644,353 which is incorporated by reference. These salts include the hydrochloride, sulfate, maleate, tartrate, citrate and the like.

In the preparation of the compositions of the invention, both drugs are micronized using conventional techniques such as air-jet milling prior to being mixed with a propellant system. The micronized active ingredients are homogenized with soya lecithin as a suspending agent prior to combining the homogenized composition with the propellant. It has been found that the effective amount of soya lecithin which provides a stable suspension of the ipratropium salt and the albuterol salt is within a narrow range which is about 0.1 to about 0.3 wt % of soya lecithin based on the total weight of the ipratropium salt, albuterol salt, propellants and the soya lecithin. Greater amounts of soya lecithin may be employed if the preparation of a stable formulation is the only consideration. However, from a pharmacological perspective, only the minimum effective amount should be employed in order to minimize any untoward effect to a patient that the soya lecithin may directly cause or any indirect effect that the use of an excess of the soya lecithin may cause in disrupting the absorption of ipratropium bromide and albuterol sulfate in the lungs of a patient. Generally, as the soya lecithin concentration increases, the level of pulmonary deposition decreases.

It has been observed that when an ipratropium salt such as the bromide is suspended with albuterol (base) and 0.1 to 0.2 wt % soya lecithin, the composition becomes unstable after about 2 months. The unstability results in the formation of agglomerates of the active drugs and soya lecithin which may tend to partially clog the aerosol valve and/or interfere with the pulmonary deposition of the active drugs by altering the site of alveolar deposition.

If from about 0.1 to 0.3 wt % soya lecithin is combined with ipratropium bromide and albuterol sulfate and a propellant mixture, a stable aerosol composition is formed which is stable in aerosol containers for at least 18 months.

In a preferred embodiment, the aerosol formulation contains a sufficient amount of ipratropium bromide and albuterol sulfate to simultaneously deliver, from the mouthpiece of the aerosol container, an effective combined dose of ipratropium bromide and albuterol sulfate which will provide bronchodilation to a patient who is afflicted with bronchospasm which is associated with chronic obstructive pulmonary disease including chronic bronchitis and emphysema.

It has been found that it is convenient to provide a concentration of ipratropium bromide and albuterol sulfate which will deliver from the mouthpiece of the aerosol device, by a single activation of the metering valve, 18 µg of ipratropium bromide and 103 µg of albuterol sulfate. The patient may be instructed to repeat the dose in order to provide the full adult dosage of the ipratropium bromide and albuterol sulfate. The dose may be adjusted depending on the therapeutic objective of the use of the active agents and the age and condition of the patient.

The propellant may be any physiologically acceptable compound which is a gas at room temperature but is easily liquefied. The propellants will preferably comprise a combination of a relatively low boiling chlorofluorocarbon (CFC) as a propellant, such as, for example CFC 12 ($CCl_2F_2$, $T_b/°C.=-29.8$) or CFC 114 ($C_2Cl_2F_4$, $T_b/°C.=-3.8$), and a relatively high boiling CFC, such as for example CFC 11 ($CCl_3F$, $T_b/°C.=23.75$). These propellants are preferred because they promote pulmonary deposition of solid drugs that are administered from aerosol containers.

The procedure for preparing the aerosol composition comprises first preparing a product concentrate which comprises the active medicaments in micronized form with a portion of the relatively high boiling CFC, such as for example CFC 11 ($CCl_3F$, $T_b/°C.=23.75$) and an aerosol grade of soya lecithin. This product concentrate is homogenized at ambient temperature and pressure, using a conventional rotor/stator homogenizer. After the product is homogenized, the homogenized product and the balance of the high boiling CFC and the relatively low boiling CFC propellants are introduced into a pressure vessel, where they are mixed under suitable conditions of temperature and pressure to form a completed and homogenous formulation. The completed formulation is then filled into aerosol containers which are provided with metered valves under elevated pressure and ambient pressure (by back filling through the valves of capped containers), or at reduced temperature and ambient pressure (wherein the containers are filled and then capped). The metered valves and methods of making aerosol compositions are well known and are described in Remington's Pharmaceutical Sciences, 1985 Ed, Mack Pub. Co., Easton, Pa., pp 1662–1677 which is incorporated by reference.

The composition of the invention is used for the same conditions that the prior art ipratropium bromide aerosol product and the prior art albuterol sulfate product are used for as set forth in the relevant sections of the 1994 Physicians Desk Reference, which is incorporated by reference.

The following Example provides a formulation according to the invention and is intended only to illustrate but not to limit the invention:

EXAMPLE

The following ingredients are used to prepare an 700 kg batch of a composition according to the invention:

| | |
|---|---|
| ipratropium bromide, monohydrate, micronized | 0.210 kg |
| albuterol sulfate, USP micronized | 1.200 kg |
| soya lecithin, aerosol grade | 1.400 kg |
| trichloromonofluoromethane | 174.936 kg* |
| dichlorodifluoromethane | 382.945 kg* |
| dichlorotetrafluoroethane | 163.155 kg* |

*This quantity includes an overage of propellant introduced during processing to compensate for vapor which remains in the sealed manufacturing tank as the liquid bulk suspension is depleted during filling.

A concentrate is prepared by combining the active drugs, the soya lecithin and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| ipratropium bromide, monohydrate, micronized | 0.0021 kg |
| albuterol sulfate, USP | 0.0120 kg |

-continued

| | |
|---|---|
| micronized soya lecithin, aerosol grade | 0.0140 kg |
| trichloromonofluoromethane | 1.6939 g |
| dichlorodifluoromethane | 3.7014 g |
| dichlorotetrafluoroethane | 1.5766 g |
| total | 7.0000 g |

Aerosol test formulations were prepared which contained:
(a) ipratropium bromide, albuterol (base), 0.1% soya lecithin;
(b) ipratropium bromide, albuterol sulfate, 0.1% soya lecithin;
(c) ipratropium bromide, albuterol (base), 0.2% soya lecithin;
(d) ipratropium bromide, albuterol sulfate, 0.2% soya lecithin;
(e) ipratropium bromide, albuterol (base), 0.5% oleic acid;
(d) ipratropium bromide, albuterol sulfate, 0.5% oleic acid;
Controls
(f) ipratropium bromide, 0.1% soya lecithin;
(d) albuterol sulfate, 0.1% soya lecithin;

Each formulation was prepared with the same propellant mixture (trichloromonofluoromethane; dichlorodifluoromethane and dichlorotetrafluoroethane and placed in two different multidose aerosol containers that were provided with a metered valve. Samples from each batch were filled into glass and aluminum containers. The formulations were stored at 30° C./45% relative humidity and were evaluated for physical stability on a monthly basis. The results of the test in the glass containers is shown in Table 1 and the result of the test in the aluminum containers is shown in Table 2:

TABLE 1

Appearance (30° C./45% RH) Glass Vials Time (months)

| Formulation | 0 | 1 | 2 | 3 | 5 |
|---|---|---|---|---|---|
| Albut. SO₄/ Ipratrop.Br 0.2% Soy lec | ++ | ++ | ++ | ++ | ++ |
| Albut. SO₄/ Ipratrop.Br 0.1% Soy lec | ++ | + | + | + | + |
| Albut. Base/ Ipratrop.Br 0.2% soy lec | + | + | + | — | — |
| Albut. SO₄/ Ipratrop.Br 0.1% Oleic acid | ++ | + | + | — | — |
| Albut. SO₄/ Ipratrop.Br 0.5% Oleic acid | + | — | — | — | — |
| Albut. Base/ Ipratrop.Br 0.5% Oleic acid | — | * | | | |
| Controls | | | | | |
| Ipratrop.Br 0.1% Soy lec | ++ | ++ | ++ | ++ | ++ |
| Albut. SO₄ 0.2% Soy lec | ++ | ++ | ++ | ++ | ++ |

Legend
++ good, conforms
— bad, does not conform
*test discontinued

TABLE 2

Appearance (30° C./45% RH) Aluminum Cans Time (months)

| Formulation | 0 | 1 | 2 | 3 | 5 |
|---|---|---|---|---|---|
| Albut. SO₄/ Ipratrop.Br 0.2% Soy lec | ++ | + | + | + | — |
| Albut. SO₄/ Ipratrop.Br 0.1% Soy lec | ++ | — | — | — | — |
| Albut. Base/ Ipratrop.Br 0.2% Soy lec | ++ | — | + | — | — |
| Albut. Base/ Ipratrop.Br 0.1% Soy lec | ++ | + | — | — | — |
| Albut. SO₄/ Ipratrop.Br 0.5% Oleic acid | ++ | — | + | — | — |
| Albut. Base/ Ipratrop.Br 0.5% Oleic acid | — | * | | | |
| Controls | | | | | |
| Ipratrop.Br 0.1% Soy lec | ++ | + | ++ | ++ | — |
| Albut. SO₄ 0.2% Soy lec | ++ | + | + | + | — |

Legend
++ good, conforms
— bad, does not conform
*test discontinued

The formulations that were based on ipratropium bromide and albuterol (base) with soy lecithin showed the presence of brown deposits near the liquid vapor interface.

I claim:

1. An aerosol formulation which comprises an effective amount of a micronized pharmaceutically acceptable salt of ipratropium and an effective amount of a micronized pharmaceutically acceptable salt of albuterol with an effective amount of soya lecithin as a suspending agent and a propellant.

2. An aerosol formulation as defined in claim 1 wherein the propellant comprise a mixture of trichloromonofluoromethane; dichlorodifluoromethane and dichlorotetrafluoroethane.

3. An aerosol formulation as defined in claim 2 which contains from 0.1 to 0.3 wt % of soya lecithin based on the combined weight of the pharmaceutically acceptable salt of ipratropium, the pharmaceutically acceptable salt of albuterol, the weight of the soya lecithin and the weight of the propellant.

4. An aerosol formulation as defined in claim 1 wherein the pharmaceutically acceptable salt of ipratropium is ipratropium bromide.

5. An aerosol formulation as defined in claim 1 wherein the pharmaceutically salt of albuterol is albuterol sulfate.

6. An aerosol formulation as defined in claim 1 which contains from 0.1 to 0.3 wt % of soya lecithin based on the combined weight of the pharmaceutically acceptable salt of ipratropium, the pharmaceutically acceptable salt of albuterol, the weight of the soya lecithin and the weight of the propellant.

7. An aerosol formulation which consists essentially of an effective amount of a micronized ipratropium bromide, an effective amount of micronized albuterol sulfate, an effective amount of soya lecithin as a suspending agent and a propellant which consists essentially of a mixture of trichloromonofluoromethane; dichlorodifluoromethane and dichlorotetrafluoroethane, wherein the effective amount of the soya lecithin is from 0.1 to 0.3 wt % of soya lecithin based on the combined weight of the ipratropium bromide, the albuterol sulfate, the weight of the soya lecithin and the weight of the trichloromonofluoromethane; dichlorodifluoromethane and dichlorotetrafluoroethane.

8. An aerosol formulation as defined in claim 7 wherein the effective amount of soya lecithin is about 0.1 wt %.

9. An aerosol formulation as defined in claim 7 wherein the effective amount of soya lecithin is about 0.2 wt %.

10. A method of formulating a stable aerosol formulation of a micronized pharmaceutically acceptable salt of ipratropium and a micronized pharmaceutically acceptable salt of albuterol, said method comprising combining a micronized pharmaceutically acceptable salt of ipratropium with micronized a pharmaceutically acceptable salt of albuterol, an effective amount of soya lecithin and a propellant.

11. A method of formulating a stable aerosol as defined in claim 10 wherein the pharmaceutically acceptable salt of albuterol is albuterol sulfate.

12. A method of formulating a stable aerosol formulation as defined in claim 10 wherein the pharmaceutically acceptable salt of ipratropium is ipratropium bromide.

13. A method of formulating a stable aerosol as defined in claim 12 wherein the pharmaceutically acceptable salt of albuterol is albuterol sulfate, the effective amount of soya lecithin is from 0.1 to 0.3 wt % based on the combined weight of the ipratropium bromide, a pharmaceutically acceptable salt of albuterol, the weight of the soya lecithin and the weight of the propellant.

14. A method of formulating a stable aerosol as defined in claim 13 wherein the propellant comprises a mixture of a mixture of trichloromonofluoromethane; dichlorodifluoromethane and dichlorotetrafluoroethane.

* * * * *